United States Patent [19] [11] Patent Number: 4,804,273
Tondello et al. [45] Date of Patent: Feb. 14, 1989

[54] METHOD AND APPARATUS FOR PARTICULATE MATTER DETECTION

[76] Inventors: Giuseppe Tondello, Via Palermo, 39, Padova; Maurizio Vincenzi, Via Rovereto, 38, Castelfranco Veneto, Treviso, both of Italy

[21] Appl. No.: 162,180

[22] Filed: Feb. 29, 1988

Related U.S. Application Data

[63] Continuation of Ser. No. 60,033, Jun. 9, 1987, abandoned.

[51] Int. Cl.⁴ ............................................. G01N 21/90
[52] U.S. Cl. .................................... 356/427; 250/574; 356/336
[58] Field of Search ............... 356/427, 336, 337, 338, 356/339; 250/574

[56] References Cited

U.S. PATENT DOCUMENTS

| | | | |
|---|---|---|---|
| Re. 28,984 | 9/1976 | Drinkuth et al. | 356/427 |
| 2,531,529 | 11/1950 | Price | 356/427 |
| 3,576,442 | 4/1971 | Nakamura | 356/427 |
| 3,858,851 | 1/1975 | Ogle | 356/427 |
| 3,966,332 | 6/1976 | Knapp et al. | 356/427 |
| 4,028,553 | 6/1977 | Farcinade | 356/427 |
| 4,402,612 | 9/1983 | Alexander et al. | 356/427 |
| 4,623,252 | 11/1986 | Hollenbeck | 356/427 |

Primary Examiner—Richard A. Rosenberger
Attorney, Agent, or Firm—Eugene E. Renz

[57] ABSTRACT

A method and apparatus is disclosed for detecting the presence of particulate matter in liquids intended for pharmaceutical use, for example liquid contained in vials, flasks or ampoules. The method involves mechanically imparting to the vial or flask a rotary motion and then suddenly stopping it. Any particles contained in the liquid will continue to move, and will be illuminated by a number of parallel light beams of laser light, which are caused to pass through the liquid. Laser light diffused by particles in the liquid is converted into an electrical signal by a photomultiplier. The signal from the photomultiplier is amplified, filtered, and compared with a reference signal. The apparatus has a number of mandrel/chuck units which each impart a rotary motion to one container. At a second location, the light from a He-Ne laser is conveyed through optical fibers in the form of several parallel beams through each container, illuminated from below through a plurality of holes in the bottom of the mandrel. The laser light diffused by the particles is detected by a photomultiplier, whose signal is processed by an electronic circuit to indicate those vials containing particulate matter.

15 Claims, 4 Drawing Sheets

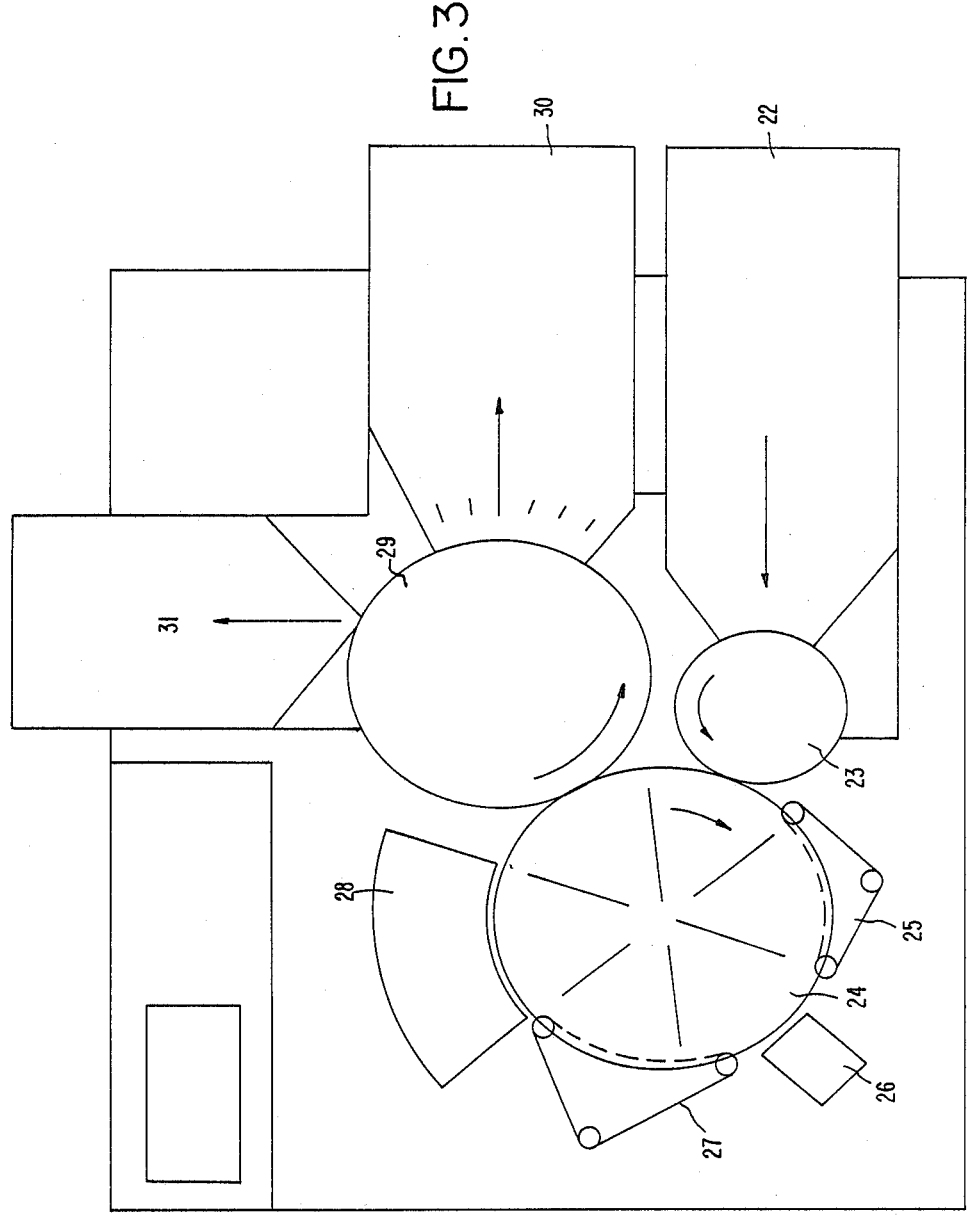

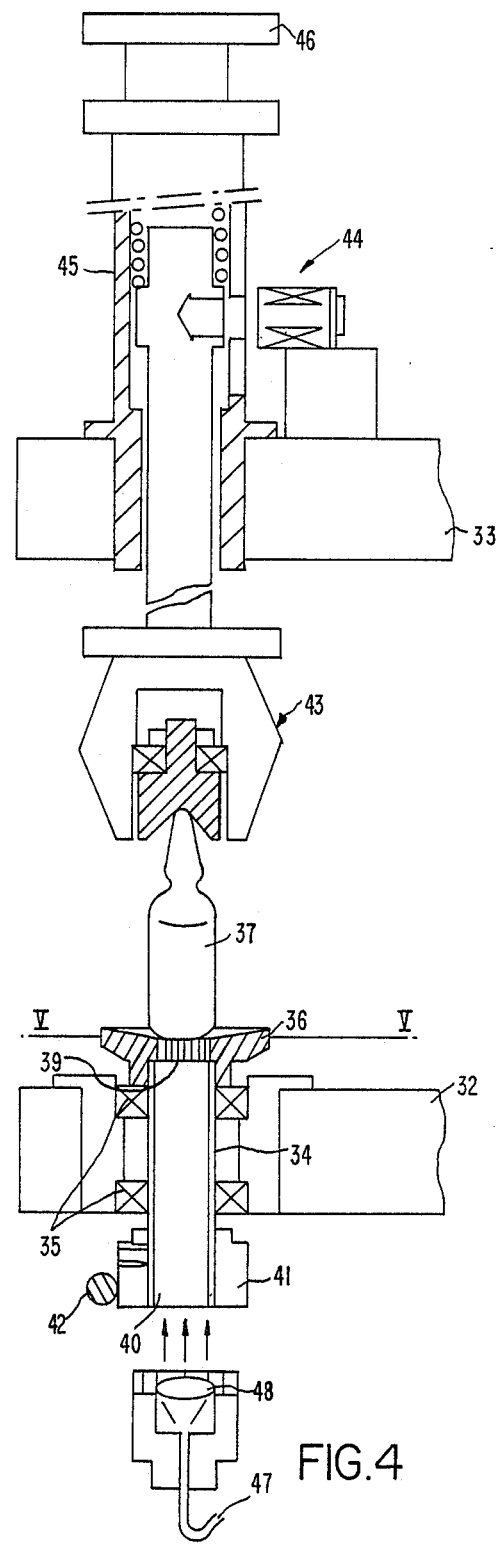
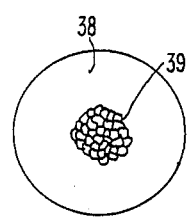
FIG.5
FIG.4

METHOD AND APPARATUS FOR PARTICULATE MATTER DETECTION

This is a continuation of application Ser. No. 060,033 filed on June 9, 1987, still pending, which is a continuation of 938,387 filed Dec. 5, 1986, now abandoned, which is a continuation of 671,752, filed Nov. 15, 1984, now abandoned.

BACKGROUND OF THE INVENTION

1. Field of the Invention

The process and apparatus described herein relates to devices for the detection of contaminant particles contained in vials or flasks, and particularly for the detection of particulate matter in liquids intended for pharmaceutical use.

2. Background Information

In the pharmaceutical industry, vials containing parenteral substances and flasks containing liquids for intravenous infusion must be inspected to determine the presence of undesirable solid particles in the liquid. This determination is a very important problem, and until now a delicate and time consuming process.

With current techniques, inspection of individual containers prior to their packaging is performed either manually or automatically by means of suitable machines. In machines for manual inspection, the vials or flasks are made to rotate very rapidly after being inserted between a mandrel and chuck arrangement that is free to rotate. After a certain period of time, the containers are abruptly stopped, and a beam of light illuminates the container, either from below or laterally, so that an operator can manually observe any particles set in motion by the residual motion of the fluid. Such a manual process is particularly inconvenient, imprecise and costly.

Prior automatic machines used to detect spurious solid particles involved transmitting an image of the container on a television picture tube or onto an array of photodiodes. In the former, after the container's rotation is stopped in a fashion similar to the manual process, the picture tube captures various images of the container in rapid succession. Every image is stored in memory in an electronic computer, and then compared among themselves point by point. If differences among the various images are detected, this signifies that the liquid contains particles which are successively occupying different positions, and the container is consequently discarded.

In machines used currently, illumination of the vial can occur through the bottom of the container, in which case the particles become the source of a diffused light which generates the visible image. In other cases, light is emitted coincident with the direction of observation, in which case the presence of the particles produces a darkening of the image at those points where they are located. In any case, the use of visible light, i.e. wide-band spectrum radiation, also requires consideration and protection from interfering ambient light sources such as room light. In the past, covers, tinted shields, or other protective measures were necessary to ensure efficiency.

In machines where the image is displayed on an array of photodiodes the number of points in the image that need to be placed in memory is reduced. In this case, however, what is inspected is not the entire container but only a portion of it, generally concentrated around the axis of rotation and of a length equal to the height of the meniscus. This involves a reduction in the system's probability of detection, since on the one hand the positions of the particles within the liquid are random, and on the other, the detector element is concentrated only on a partial area of the liquid itself. This problem has been overcome by performing two inspections at two independent and successive inspection stations. The containers discarded are those which show the presence of particles at least at one of the two observation stations.

The methods described, even allowing a sufficient level of reliability in inspection, require complex and expensive electronic components such as vidicon-type or solid-state type television cameras, photodiode arrays, fast analog-digital converters, and high-speed computers to record and compare the images.

It should be remembered that to be profitable, a container inspection machine must be capable of inspecting several thousands of units per hour.

SUMMARY OF THE INVENTION

The purpose of our discovery is to devise a process which makes it possible to detect particles in liquids contained in vials or flasks in an automatic and rapid manner. Consequently, the primary object of the invention is a device capable of detecting and analyzing a signal reflecting the presence of particles in a liquid quickly and accurately.

Another object of the invention is to produce an apparatus which allows the detection of particles located anywhere in the entire volume of of the liquid, and not only in a small portion of it.

A further object of the invention is to provide a device for detecting particulate matter in liquids, which is relatively simple and of a minimum cost.

A still further object of the invention is to produce equipment with high sensitivity, for the detection of even very small particles.

These and other objects, which will more clearly emerge in the following discussion, are realized in a method for the detection of contaminant particles contained in vials or flasks of liquid for pharmaceutical use, characterized by a sequence of steps involving:

a. rotating the flask and abruptly stopping its motion after a predetermined time;

b. illuminating the flask, preferably from below, with a number of beams of light produced by a laser, whereby the light is diffused by particulate matter suspended in the liquid;

c. detecting the diffused light with a photomultiplier, which produces an electrical signal reflective of the light received;

d. filtering the signal from the photomultiplier to obtain that portion of the signal which is truly reflective of laser light diffused by particulate matter and comparing it with a reference signal; and e. rejecting those flasks whose photomultiplier signal indicates an unacceptable amount of particulate matter.

The word "flask" as used herein will be understood to include any suitable flask, vial, ampoul, or other container for holding liquid requiring inspection for particulate matter.

The objects of the invention are also realized in an apparatus for the detection of particulate matter contained in vials or flasks of liquid for pharmaceutical use, including:

a. a unit for rotating a flask consisting of cooperating chuck and mandrel members for grasping the flask, and a motor, mechanically connected to the mandrel member, for providing and stopping rotation of the flask, the mandrel member having a plurality of holes therethrough;

b. a laser light source;

c. a fiber optic bundle positioned to transmit laser light from the source to the holes in the mandrel, such that a plurality of columns of laser light are transmitted through the flask;

d. a photomultiplier positioned with respect to the flask for detection of laser light diffused by particulate matter passing through the columns of laser light and for generating an electrical signal reflective of the light detected; and e. an indication device connected to receive the electrical signal from the photomultiplier, for indicating when particulate matter has been detected.

A rejection device can also be incorporated for segregating those flasks in which particulate matter has been detected.

BRIEF DESCRIPTION OF THE DRAWINGS

Further characteristics and advantages of the invention will be seen better in a detailed description of a preferred embodiment, given as a non-limiting example, and illustrated by the attached sheets of drawings in which:

FIG. 3 shows a schematic view of a particulate matter detection device indicating the general location and relation of various of the components of the overall apparatus;

FIG. 4 shows a detailed partially sectional view of a single unit for insertion and rotation of flasks; and FIG. 5 shows a section view taken along V—V of FIG. 4.

DETAILED DESCRIPTION OF THE PREFERRED EMBODIMENT

Figure 1:
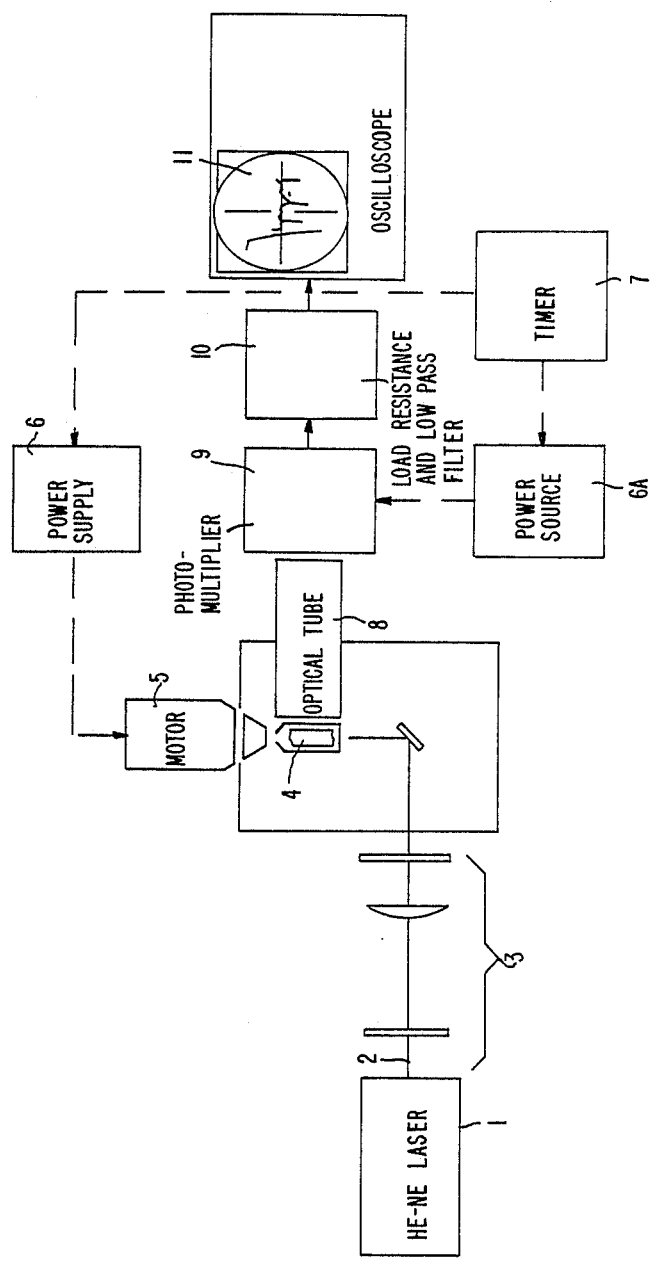
FIG. 1 shows a block diagram of the detection system of the instant invention.

Referring to the figures mentioned, the method which is the subject of this invention generally consists in mechanically rotating a vial or flask for a length of time sufficient for all the liquid contained therein to rotate, together with any particles contained within it. The container's rotation is then abruptly stopped, and it is conveyed to a detection and inspection unit where the vial or flask is illuminated from below by a He-Ne laser beam. The laser beam is previously made to pass through a baseplate provided with small holes so that it forms a number of small parallel beams arranged side by side passing through the vial or flask. The beams illuminate the particles contained in the liquid, and the latter diffuse the laser light. Diffused laser light is collected by an assemblage of lenses which projects the light onto a photomultiplier which converts it into an electrical signal.

The particles are in motion, and are therefore alternately illuminated by one of the beams of laser light which pass through the liquid. The signal collected by the photomultiplier is therefore, as far as the light diffused by the particles is concerned, a signal which contains an alternating component. The alternating component can be discriminated by means of suitable electronic filtering from a continuous component which is also always present in the signal from the photomultiplier. Such continuous component is produced by light diffused from the glass of the vial or the container, marks on the container, imperfections and scratches on the glass, the meniscus of the liquid, or by the liquid itself if it is fluorescent. All of these contributions to the diffused signal are substantially constant and therefore generate a relatively continuous component.

The composite signal output by the photomultiplier, after appropriate amplification, is divided into its continuous component and its alternating component. The latter component contains the signal of interest, produced by the particles which diffuse the laser light, as well as a noise factor. The alternating component is passed through a discriminator to remove the noise factor, whose threshold level varies as a function of the square root of the value of the continuous component. This threshold level produces an automatic compensation between the value of the diffused signal, the amplitude of the noise and the amplitude of the peaks, even for containers that are very dissimilar in terms of optical characteristics. The signal thus obtained is then integrated over a preselected time and compared with an externally applied reference signal, depending on the product being analyzed, which gives the reference between acceptable and rejected containers.

To obtain maximum contrast in particle detection, the laser radiation which illuminates the bottom of the container is spatially modulated in the manner we have just discussed, by dividing the primary beam into a number of small parallel beams so as to create, within the container, zones of light and dark which produce the modulation of the diffused-light signal. With this process, it is possible to use a succession of electronic filters with cutoff frequencies of a few hundred Hz, which is very advantageous in terms of the signal to noise ratio of the system, to segregate that portion of the composite signal directly attributable to particulate matter contained in the liquid being inspected. In addition, this process produces illumination and detection of diffused light from particles anywhere within the entire volume of the liquid contents.

The laser light used in both the method and apparatus is, as known, highly polarized and monochromatic. By using the first of these characteristics, it is possible to enhance the phenomenon of diffusion by particulate matter by suitably orienting the direction of polarization with respect to the direction of diffusion. Exploiting the second characteristic, a very narrow-band interference filter is placed in front of the photomultiplier. This narrow-band filtering allows the passage of the monochromatic diffused radiation, but effectively blocks other wide-band spectrum radiation such as that from ambient light. It is therefore easier to proceed even in the presence of normal levels of ambient light.

Referring to FIG. 1, the apparatus consists essentially of a He-Ne laser 1 which generates a beam of light 2 which, through an optical train 3 or fiber optic bundle, is made to illuminate from below a vial or flask 4 which is made to spin rapidly and is then stopped by a motor 5 equipped with a power supply 6 controlled by a timer 7. The assembly for holding and rotating flask 4 is described in greater detail in relation to FIG. 4.

The light diffused by the particles present in flask 4 is collected and projected by an optical tube 8, which consists of any known arrangement of lenses for projecting the diffused light from the flask 4, onto photomultiplier 9 which converts the light into an electrical signal. Photomultiplier 9 receives power from high voltage power source 6a. Source 6a is also controlled by timer 7, such that no power is supplied to photomultiplier 9 when timer 7 enables power supply 6 to turn motor 5, turning flask 4. The electrical signal from photomultiplier 9 passes to an electronic processing device 10 which is shown to be equipped with an oscilloscope 11.

Figure 2:
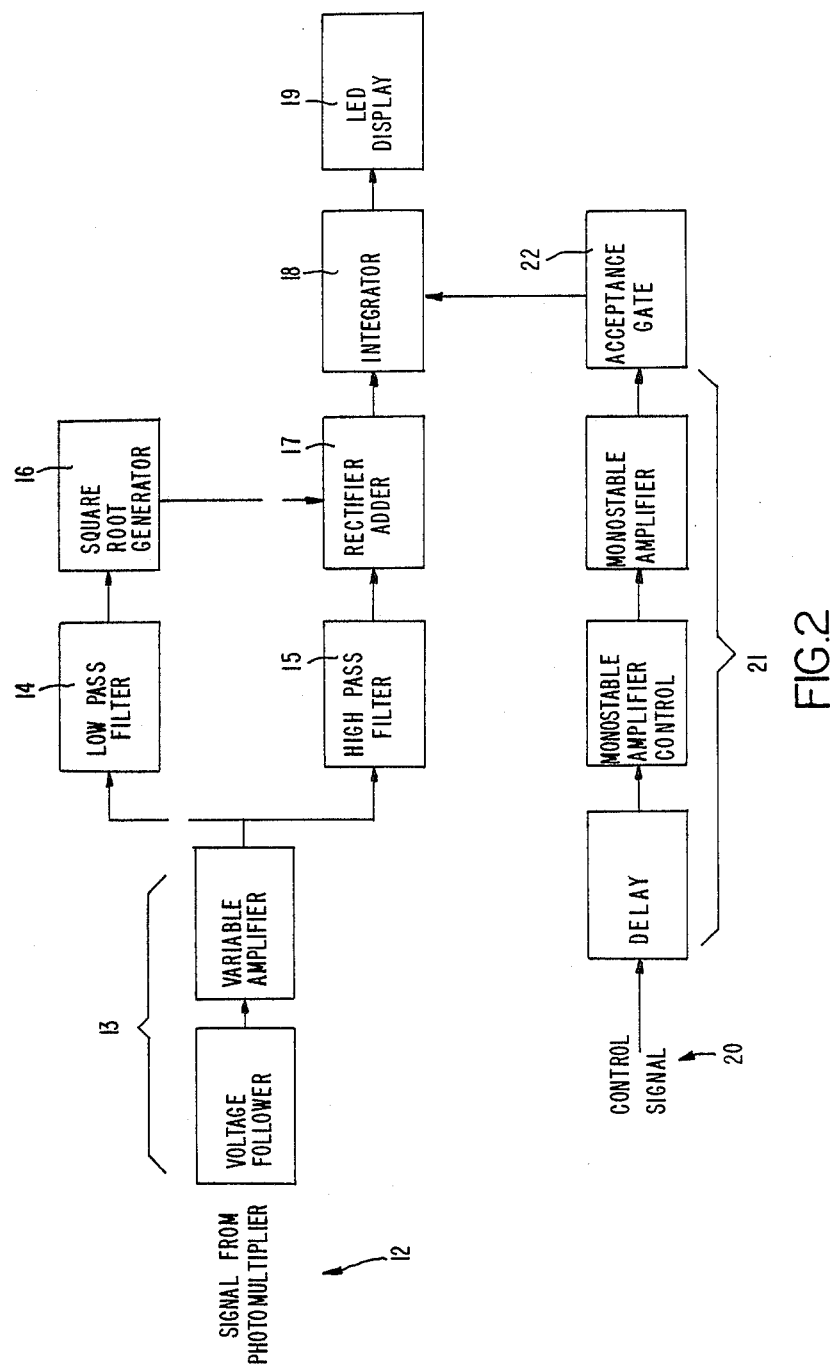
FIG. 2 shows a block diagram of the system for processing the signal output by the photomultiplier shown in FIG. 1.

FIG. 2 shows more clearly how the signal output by photomultiplier 9 is processed. The signal is first processed and amplified by a voltage follower and variable amplifier arrangement 13. Since such arrangements are known in the art, the specific details of the electronic circuits have been omitted from this application. The continuous component of the photomultiplier signal is separated from the variable component by low-pass filter 14 and eliminated from the photomultiplier signal by high-pass filter 15. At the output side of low-pass filter 14 the continuous voltage signal is reduced to its square root value by means of element 16, which element can be any suitable electronic means. This value serves as the noise threshold value for rectifier adder 17 which operates in a known manner on the alternating component of the photomultiplier signal. The now relatively isolated alternating component, which is reflective of particulate matter in flask 4, passes to integrator 18 and is displayed by suitable means on LED display 19.

A control signal 20, processed by an electronic circuit 21, constitutes a reference signal at the acceptance gate 22, where it is compared with the output of integrator 18. If the comparison determines that flask 4 contains unacceptable particulate matter, a signal is generated by gate 22 for rejecting such flask.

With regard to the mechanical apparatus for performing the inspection procedure, as illustrated in FIG. 3, this is composed of a loading surface made up preferably of an inclined conveyor belt to allow pickup of the containers or vials, which feeds to a loading star wheel 23 which picks up the containers from the loading surface and inserts them in transport unit 24. Transport unit 24 consists of six rotation units, which are illustrated in detail in FIG. 4, each of which suppport a flask 4 at top and bottom, allowing it to rotate.

The vials or flasks are given a first rotary motion by means of a first motorized belt 25. In cases where vials are being inspected, the function of this initial rotation is to eliminate the presence of liquid in the upper part or tip of the vial. In practice, the first rotation also has the purpose of rinsing the inside of the container so that any particles adhering to the upper sides of the vial, which are not normally contacted by the liquid, are dispersed in the liquid for subsequent detection.

After this first belt 25, comes a synchronization unit which generates the electrical signals required for proper synchronization of the various phases of the overall inspection system, such as detection of the presence of the container, initiation of the observation cycle, end of the observation cycle, the reject phase, and counting pulses used to coordinate such synchronization.

After synchronization unit 26 comes a second motorized belt 27, whose function is to impart a second rotation to the vial or container, the purpose of which is to optimize turbulence of the particles suspended in the liquid in the container.

After this belt area 26 is the detection and inspection unit 28 which, through a fiber optics bundle, transmits a beam of laser light directly below the individual vials.

This detection unit is composed of a photomultiplier which is placed beside the container, and is also equipped with the assemblage of electronic circuits which process the signal according to the apparatus illustrated in connection with FIGS. 1 and 2. It will be appreciated that it may be desirable to inspect more than one vial at a time to increase the output rate. In such a situation, a series of photomultipliers would be incorporated with one photomultiplier positioned adjacent to each vial being inspected.

After this detection and inspection unit 28 comes an unloading star wheel 29 with two exit chutes, for acceptable vials 30, and for rejected vials 31.

Referring to FIG. 4, the transport unit 3 is shown to be composed of a first lower plate 32 combined with a second upper plate 33. The first lower plate supports a lower spindle 34 which is mounted on the plate 32 by means of bearings 35 which allow it to rotate freely. This spindle 34 has at the top a mandrel 36 having a depression on which the vial 37 is placed. As seen more clearly in FIG. 5, the depression is formed in base 38 of mandrel 36 and is equipped with a number of small holes 39 which connect to a hollow cavity 40. Below spindle 34 is a cylindrical member 41 contacted by the belt 42. Belt 42 is for illustration only, as it will be appreciated that cylindrical member 41 contacts first belt 25, second belt 27, and a fixed belt located at the point of inspection for stopping the rotation of the flask.

Above, on second plate 33, is placed a counter-spindle or chuck 43 whose height can be adjusted by means of an adjustment cam 44 and which chuck is pressed down by a spring 45 whose compression is controlled by an axial screw 46.

The vial 37 is inserted in the space between mandrel 36 and chuck 43 and is forced to rotate along with them when chuck 43 moves down onto vial 37. From below, an optical fiber 47 transmits a portion of the laser beam to an optical assembly 48, which emits a parallel beam which is then divided into a number of small beams by the holes 39. It is advantageous to use a single laser light source which, by means of optical fibers such as those indicated by 47, is transmitted to a number of detection stations so that multiple readings can be made.

The description and illustrations show that all of the proposed objects have been attained, and show particularly that a procedure has been developed for the detection of particles contained in vials or other containers which is simple, automatic and reliable, as well as very fast. The equipment which performs the procedure is also very simple and inexpensive.

Working from the same invention concept, there might be other different ways of realizing the method in question, and in the apparatus, devices equivalent to those illustrated could be used; these modifications, however, would remain within the scope of the invention. Materials, components and dimensions might be of any magnitude or type, depending on requirements.

We claim:

1. An apparatus for detecting particulate matter suspended in a liquid, which liquid is contained in a flask, comprising:

a unit for rotation of the flask about an axis of rotation, comprising cooperating chuck and mandrel members for grasping the flask and a motor mechanically connected to the mandrel member for providing and stopping rotation of the flask about said axis, said mandrel having a plurality of holes therethrough;

a laser beam source;

a fiber optic bundle positioned to transmit laser light from the source to the holes in the mandrel, such that a plurality of columns of laser light are transmitted through the flask and generally parallel to said axis;

a photomultiplier positioned with respect to the flask for detection of laser light diffused generally radially away from said axis by particulate matter passing through the columns of laser light and for generating an electrical signal reflective of the light detected; and indication means, connected to receive the electrical signal from the photomultiplier, for indicating when particulate matter has been detected.

2. The apparatus of claim 1, wherein the laser comprises He-Ne type laser.

3. Apparatus as in claim 1, wherein the unit for rotation of the flask comprises two opposed parallel plates comprising a lower plate having a number of mandrels for supporting flasks and the upper plate having corresponding locking chucks.

4. Apparatus as in claim 3, wherein the lower mandrel is concave, with a support on its upper surface for the flask, and which has a number of holes passing therethrough, said holes serving to transmit the laser light through the liquid as a number of small parallel beams of laser light.

5. Apparatus as in claim 4, wherein the mandrel is brought into contact with a motor-driven belt, said belt producing rotation of the mandrel, flask and chuck.

6. Apparatus as in claim 5, wherein the plates supporting the mandrels and chucks rotate in step, so as first to bring the mandrels in contact with the actuating belt and then to bring the vials to a detection station where a number of mandrels are illuminated simultaneously from below by a beam of laser light, there being present at said detection station several photomultipliers each associated with a single flask for detecting the light diffused by the particles suspended in the liquid and in motion.

7. Apparatus as in claim 6, further comprising following said detection station, an assembly for removing the examined flasks, said assembly providing two exit routes, one for flasks considered acceptable and a second for flasks to be discarded, the two routes being chosen on the basis of the signal that has been processed and compared.

8. Apparatus as in claim 3, wherein the chuck member is mounted with bearings on the upper plate and is capable of axial movement along its axis of rotation, said movement being controlled by a cam follower connected to the chuck, and an adjustable spring pressing the cam follower against a cam which allows the chuck to move axially against the upper part of the flask so as to immobilize it between the chuck and the mandrel.

9. A method for detecting contaminant particles in vials of liquid intended particularly for pharmaceutical use, comprising the steps of:

imparting a rotary motion to the vial about an axis of rotation and stopping the motion abruptly after a predetermined time;

illuminating the vial by means of a plurality of light beams generally parallel to said axis and produced by a laser, whereby the laser light is diffused by particulate matter suspended in the liquid;

detecting the light diffused generally radially away from said axis by means of a photomultiplier, which produces an electrical signal of reflective light received;

filtering the signal from the photomultiplier to obtain that portion of the signal which is reflective of laser light diffused by particulate matter and comparing it with a reference signal; and identifying those vials whose photomultiplier signal indicates an unacceptable amount of particulate matter.

10. The method of claim 9, further comprising the step of initially rotating the vials to provide for washing of the internal surfaces which are not normally wetted by the liquid, thus also suspending in the liquid those particles which might be adhering to the sides, prior to rotating the vials in Step A.

11. The method of claim 9, wherein the inspection does not begin until the meniscus of the liquid generated by the rotation has completely settled.

12. The method of claim 9, wherein the vial is illuminated by a number of parallel beams of laser light transmitted to the bottom of the vial through optical fibers.

13. The method of claim 9, wherein the diffused light signal from the photomultiplier is separated into a continuous component and an alternating component.

14. The method of claim 13, wherein the continuous component is reduced to its square root value which value is used as the noise cutoff threshold for isolating that portion of the component which is reflective of laser light diffused by particulate matter.

15. The method of claim 14, further comprising the step of integrating over time the isolated portion of the alternating component and comparing the integration with a reference signal, which signal is predetermined depending on the products being examined and constituting the limit of acceptability and choice between good containers and those to be discarded.

* * * * *